(12) United States Patent
Na et al.

(10) Patent No.: US 8,946,394 B2
(45) Date of Patent: Feb. 3, 2015

(54) CONJUGATE FOR PHOTODYNAMIC DIAGNOSIS OR THERAPY AND METHOD FOR PREPARING SAME

(75) Inventors: Kun Na, Gyeonggi-do (KR); Fang Yuan Li, Gyeonggi-do (KR); Byoung Chan Bae, Gyeonggi-do (KR)

(73) Assignee: Panaxem Co., Ltd., Gyeonggi-Do (KR)

( * ) Notice: Subject to any disclaimer, the term of this patent is extended or adjusted under 35 U.S.C. 154(b) by 0 days.

(21) Appl. No.: 13/877,162

(22) PCT Filed: Dec. 21, 2011

(86) PCT No.: PCT/KR2011/009967
§ 371 (c)(1),
(2), (4) Date: May 1, 2013

(87) PCT Pub. No.: WO2012/087040
PCT Pub. Date: Jun. 28, 2012

(65) Prior Publication Data
US 2013/0281679 A1    Oct. 24, 2013

(30) Foreign Application Priority Data

Dec. 21, 2010  (WO) ................ PCT/KR2010/009173

(51) Int. Cl.
*A61K 47/48* (2006.01)
*A61K 41/00* (2006.01)
*A61K 49/00* (2006.01)

(52) U.S. Cl.
CPC ......... *A61K 47/4823* (2013.01); *A61K 41/0071* (2013.01); *A61K 49/0036* (2013.01); *A61K 49/0054* (2013.01)
USPC ............................. 530/391.9; 514/54; 536/53

(58) Field of Classification Search
CPC . A61K 47/0071; A61K 47/4823; A61K 47/48
USPC ............................. 514/54; 530/391.9; 536/53
See application file for complete search history.

(56) References Cited

U.S. PATENT DOCUMENTS 7,153,841 B2 * 12/2006 Roncucci et al. ................ 514/63
2006/0116346 A1 *  6/2006 De Luca et al. .................. 514/54

FOREIGN PATENT DOCUMENTS

| JP | 2004-529171 A | 9/2004 |
| KR | 2003-0046394 A | 6/2003 |
| WO | 0209690 A2 | 2/2002 |
| WO | 02090361 A1 | 11/2002 |
| WO | 2005110388 A1 | 11/2005 |
| WO | 2010126551 A1 | 11/2010 |

OTHER PUBLICATIONS

Yip et al, Molecular Cancer Therapy, 2006, 5(9), 2139-48.*
Chatterjee et al, Advanced Drug Delivery Reviews, 2008, 60, 1627-37.*
Panyam et al, Advanced Drug Delivery Reviews, 2003, 55, 329-47.*
Fangyuan, L., et al., "Acetylated Hyaluronic Acid/Photosensitizer Conjugate for the Preparation of Nanogels with Controllable Phototoxicity: Synthesis, Characterization, Autophotoquenching Properties, and in vitro Phototoxicity against HeLa Cells", "Bioconjugate Chem.", Jun. 29, 2010, pp. 1312-1320, vol. 21.

* cited by examiner

*Primary Examiner* — Ganapathy Krishnan
(74) *Attorney, Agent, or Firm* — Hultquist, PLLC; Steven J. Hultquist

(57) ABSTRACT

The present invention relates to a conjugate of acetylated biocompatible polysaccharide and phthalocyanine-based compound for photodynamic diagnosis or therapy in which biocompatible polysaccharide is acetylated and a phthalocyanine-based compound is bound to the acetylated polysaccharide. The conjugate for photodynamic diagnosis or therapy according to the present invention is characterized in that the polysaccharide is acetylated to improve solubility in a solvent and thus enable various chemical modifications, and the conjugate may specifically target tumor cells, has superior cancer cell selecting and accumulating capacity, and has excellent effects of killing cancer cells when near infrared ray is irradiated. The conjugate of the present invention may not show cytotoxicity for cells other than cancer cells even when near infrared ray is irradiated, and thus exhibits superior in vivo stability, and therefore, may be valuably used in disease diagnosis or therapy using photodynamics.

10 Claims, 9 Drawing Sheets

Chondroitin sulfate acetate(AC-CS)-ZnPcCOOH

AcCS-ZnPc 1mg

☐ Size(nm) = 229.8 ± 4.2(PdI=0.131)

AcCS-ZnPc 2mg

☐ Size(nm) = 270.0 ± 4.7 (PdI=0.137)

US 8,946,394 B2

CONJUGATE FOR PHOTODYNAMIC DIAGNOSIS OR THERAPY AND METHOD FOR PREPARING SAME

CROSS-REFERENCE TO RELATED APPLICATIONS

This application is a U.S. national phase under the provisions of 35 U.S.C. §371 of International Patent Application No. PCT/KR2011/009967 filed Dec. 21, 2011, which in turn claims priority of PCT Patent Application No. PCT/KR2010/009173 filed Dec. 21, 2010. The disclosures of such international patent applications are hereby incorporated herein by reference in their respective entireties, for all purposes.

TECHNICAL FIELD

The present invention relates to a conjugate of acetylated biocompatible polysaccharide and phthalocyanine-based compound for photodynamic diagnosis or therapy and to a method for preparing the same, and more particularly, to a biocompatible conjugate in which the acetylated polysaccharide is bound to the phthalocyanine-based compound, capable of having superior accumulation ratio and target ratio with respect to cancer cells and exhibiting superior stability in cells other than cancer cells, and a method for preparing the same.

BACKGROUND ART

Photodynamic therapy (PDT) is a technology of treating incurable diseases such as cancer and the like or treating diseases such as acne and the like without performing an operation by using a photosensitive material (hereinafter, referred to as "photosensitizer"). PDT has been actively studied from the early 21st century, and currently, is being used in order to increase immunity in cancer diagnosis and therapy, autologous bone marrow transplantation, antibiotics, AIDS therapy, skin graft, or arthritis therapy, and thus the application range thereof has gradually widened.

In particular, as for PDT used in cancer therapy, when a photosensitizer, which is a material sensitive to light, is administered into the body and external light is irradiated, the photosensitizer chemically reacts with fluent oxygen in the external light, to generate singlet oxygen or free radical, and this singlet oxygen or free radical induces apoptosis in various lesions and cancer cells to destruct them.

Currently, porphyrin derivatives, chlorine, bacteriochlorin, phthalocyanine, 5-amino-levulinic acid derivatives, and the like, have been known as the photosensitizer used in PDT. Cyclic tetrapyrrole derivatives as the photosensitizer is characterized by being selectively accumulated in cancer cells and exhibiting fluorescence or phosphorescence due to compound property, and thus may be utilized as a reagent for early diagnosis. In addition, since metalloporphyrin in which metal is bound inside the cyclic tetrapyrrole exhibits several characteristics depending on the kind of metal bound thereto, metalloporphyrin is used as a contrasting agent at the time of magnetic resonance imaging (MRI) and thus is applied during the early diagnosis of tumor cells such as cancer cells. Also, 5-amino-levulinic acid derivatives, which are the most widely known photosensitizers, are simply used and have a small molecular weight, which thus comparatively facilitate skin permeation, and have few side effects and thus are stable. In addition, it has been reported that a metallophthalocyanine-based compound in which metal is bound to an inside of phthalocyanine in which pyrrole groups of cyclic tetrapyrrole are conjugated with benzene rings and connected via aza nitrogen, or an inside of naphthalocyanine in which each benzene ring of phthalocyanine is conjugated with another benzene ring, has higher absorption wavelength and molar absorptivity than a general porpyrin based compound.

PDT can selectively remove only cancer cells while maintaining normal cells; eliminate the risk of general anesthesia; and facilitate the operation even with simple local anesthesia alone.

However, PDT is difficult to apply to bulky tumor cells through which light does not pass. In particular, PDT has disadvantages in that the photosensitizer is slow in view of in vivo metabolism and thus remains for a long time in the body, resulting in phototoxic side effects, and scarcely accumulates in the tumor cells, resulting in decreasing the concentration of the photosensitizer in the tumor cells, failing to efficient therapy effects.

Moreover, the half-life of the photosensitizer is long, which causes patients to inconveniently stay in the lightless environment after the treatment, and the photosensitizer is difficult to accumulate in the tumor cells. In addition, treating compounds accumulate in the body for a long time including the therapy time, which causes various side effects in the body. Furthermore, most photosensitizers used for PDT are hydrophilic products, and do not easily penetrate the skin, and thus therapy needs to be implemented several times over a long period, which causes therapy to be excessively long.

Therefore, new photodynamic therapeutic agents capable of having high accumulation ratio specifically in cancer cells, minimal side effects, superior therapy effects and efficiently utilizing biocompatible polysaccharides are required to be developed.

DISCLOSURE

Technical Problem

The present invention has been made in an effort to provide a new conjugate for photodynamic diagnosis or therapy, capable of increasing the accumulation ratio of phthalocyanine-based compound as a photosensitizer in tumor cells and exhibiting cytotoxicity specifically to only cancer cells while remarkably decreasing phototoxicity due to fluorescent interference in cells other than cancer cells.

Technical Solution

The present invention was completed by complexing a phthalocyanine-based compound in which —COOH or a benzene ring substituted with —COOH is introduced to phthalocyanine or naphthalocyanine, and polysaccharide having modified chemical property, which is obtained by acetylating biocompatible polysaccharide insoluble in an organic solvent, that is, specifically, by preparing a conjugate of acetylated biocompatible polysaccharide capable of increasing the accumulating ratio of photosensitizer in the tumor cells and not exhibiting cytotoxicity due to fluorescent interference in cells other than cancer cells even when near infrared ray is irradiated, and a photosensitizer showing higher absorptivity and absorption in a near infrared region.

Therefore, the present invention provides a conjugate for photodynamic diagnosis or therapy, in which acetylated biocompatible polysaccharide is bound to a photosensitizer.

Further, the present invention provides a method for preparing a conjugate for photodynamic diagnosis or therapy, the method comprising: acetylating biocompatible polysaccharide; dissolving the acetylated biocompatible polysaccharide in an organic solvent; and adding a phthalocyanine-based compound and a catalyst to the biocompatible polysaccharide to bind the photosensitizer to the biocompatible polymer.

Advantageous Effects

The conjugate for photodynamic diagnosis or therapy according to the present invention is prepared by binding the acetylated biocompatible polysaccharide and the phthalocyanine-based compound, and can easily accumulate in cancer cells in vivo, while the materials that do not accumulate do not exhibit cytotoxicity due to fluorescent interference, even when near infrared ray is irradiated. Further, when the conjugate accumulates in the cancer cells, the bond between the biocompatible polysaccharide and the photosensitizer is disconnected by an enzyme in the cancer cell, and here, when the near infrared wavelength light is irradiated, the conjugate exhibits cytotoxicity and thus maximizes anti-cancer effects at the time of near infrared irradiation, and also, exhibits fluorescence and thus may be used for imaging.

DESCRIPTION OF DRAWINGS

FIG. 15 shows comparison in the degree of apoptosis of the unmodified Zn-Pc-COOH between when laser was not irradiated (●-) and when laser was irradiated (-○-), and FIG. 16 shows comparison in the degree of apoptosis of the conjugate of the present invention, Ac—Cs—Zn-Pc-COOH, between when laser was not irradiated (●-) and when laser was irradiated (-○-).

BEST MODE

Figure 1:
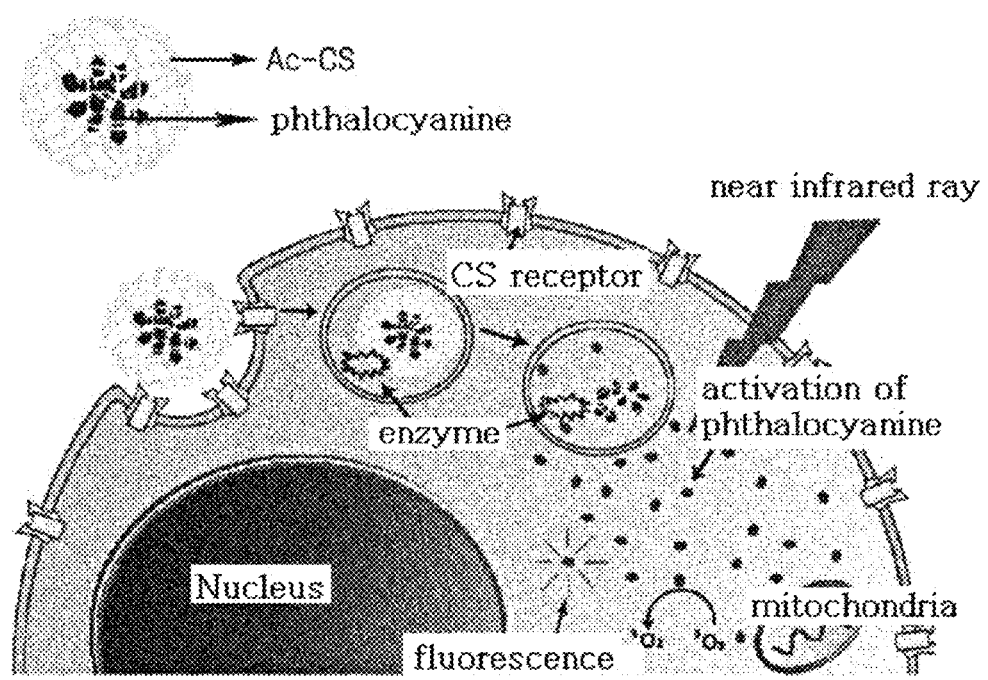
FIG. 1 is an explanation view of a mechanism showing that a biocompatible conjugate of the present invention in which a phthalocyanine-based compound is bound to acetylated biocompatible polysaccharide exhibits cytotoxicity in a cancer cell.
Figure 2:
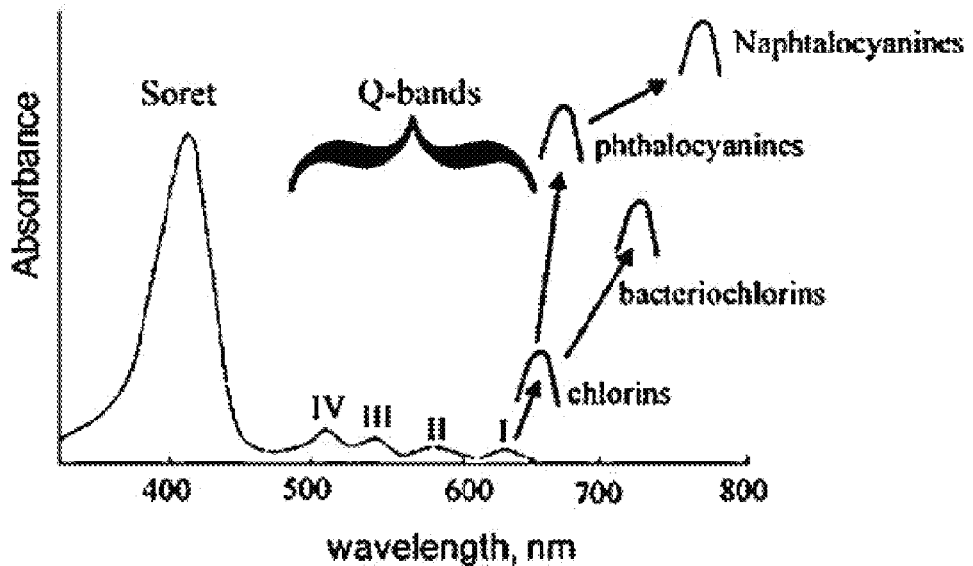
FIG. 2 is a graph showing absorbances of photosensitizers, such as phthalocyanine, naphthalocyanine, chlorin, and bacteriochlorin.

The present invention provides a conjugate for photodynamic diagnosis or therapy, in which a phthalocyanine-based compound as a photosensitizer is bound to acetylated biocompatible polysaccharide.

The conjugate of acetylated biocompatible polysaccharide and phthalocyanine-based compound for photodynamic diagnosis or therapy according to the present invention is for new photodynamic therapy method capable of increasing the accumulation ratio in cancer tissues or cancer cells and the target ratio to cancer tissues or cancer cells and remarkably decreasing phototoxicity due to fluorescent interference in cells other than the cancer tissues or the cancer cells. Thus, there is provided a conjugate for photodynamic diagnosis or therapy in which the phthalocyanine-based compound as a photosensitizer is bound to the acetylated biocompatible polysaccharide.

Generally, the biocompatible polysaccharide has good solubility in water but low solubility in an organic solvent, and thus is less soluble in the existing organic solvent, whereby this polysaccharide has difficulty in being chemically bound. However, according to the present invention, the polysaccharide is acetylated to increase solubility in the organic solvent, and allows several chemical modifications. In addition, the existing photodynamic therapeutic agent using only a photosensitizer needs to be locally administered since it has high hydrophobicity and thus is not suitable for injections, and has low accumulating efficiency and targeting efficiency with respect to cancer cells and thus does not induce fluorescent interference, which may influence even normal cells in vivo. However, according to the present invention, only the biocompatible polysaccharide itself, without a separate cancer cell targeting material, through the acetylation, binds to some target receptors among several receptors over-expressed on a surface of the cancer cell, to thereby increase the accumulating efficiency in the cancer tissue, and, later is easily decomposed by an enzyme reaction. Here, fluorescent interference is released, and in this situation, when a near infrared wavelength light is irradiated, the cancer cells can be killed.

In the present invention, the binding of the phthalocyanine-based compound and the biocompatible polysaccharide is not particularly limited so long as the binding of the phthalocyanine-based compound and the biocompatible polysaccharide can be cut by an enzyme reaction when the conjugate accumulates in the cancer cell. For example, the binding may be an amide bond, that is, a —CO—NH— bond or an ester bond, and preferable is an ester bond formed by binding the CH$_2$OH group of the biocompatible polysaccharide and the —COOH group introduced to the phthalocyanine-based compound. The reason is that the ester bond has higher decomposition efficiency in vivo as compared with other bonds including the amide bond, and thus exhibits high therapy effects by using only a small amount of photosensitizer.

In addition, the conjugate for photodynamic diagnosis or therapy according to the present invention may assume in the form of nano-gel or nano-microsphere, as a nano-sized self-assembly, which is stable in a water system, through the balance of the biocompatible acetylated polysaccharide derivative having hydrophilic property and the photosensitizer having hydrophobic property.

According to the method for preparing a conjugate in which the phthalocyanine-based compound is bound to the acetylated polysaccharide according to the present invention, the polysaccharide insoluble in the organic solvent is acetylated, so that the conjugate can be prepared by using the phthalocyanine-based compound as a photosensitizer in the organic solvent such as DMSO or formamide. Hereinafter, the method for preparing the conjugate for photodynamic diagnosis or therapy according to the present invention will be described in more detail according to the steps.

First Step: Acetylating Biocompatible Polysaccharide

In order to prepare a conjugate for photodynamic diagnosis or therapy of the present invention, first, the biocompatible polysaccharide is acetylated.

The polysaccharide needs to have superior biocompatibility and biodegradability in vivo, have superior stability in vivo, and effectively accumulate in cancer tissues.

As the polysaccharide usable in the present invention, any polysaccharide or polysaccharide derivative that can have biocompatibility in vivo may be used. For example, pullulan, hyaluronic acid, dextran, or chondroitin sulfate may be used, but the present invention is not limited thereto. In an example of the present invention, a chondroitin sulfate derivative was used.

Of the polysaccharide usable in the present invention, pullulan is a material obtained by isolating and purifying polysaccharide produced from Aureobasidium pullulans ((DE BARY) ARN.), and a main component thereof is neutral polysaccharide. Pullulan is well soluble in water but insoluble in alcohols and oils, and has lower viscosity than other gums, but is stable against acid, alkali, heat, and the like. In particular, pullulan has strong adhesive strength as well as film forming property, and has two kinds of average molecular weights, 200,000 and 100,000. In addition, pullulan has viscosity of 1~2 cps at room temperature.

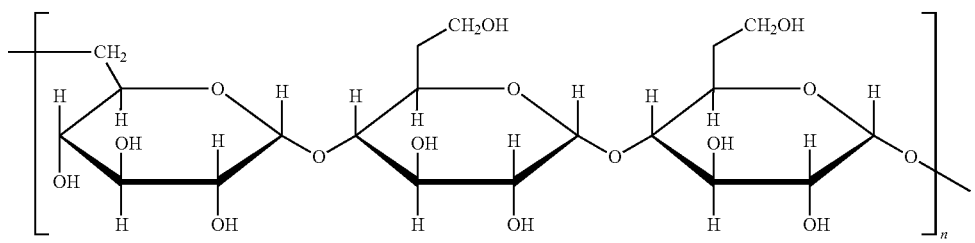

<Structural Formula of Pullulan>

In addition, polysaccharide usable in the present invention, hyaluronic acid, is known as important mucopolysaccharide, together with chondroitin sulfate and the like. Hyaluronic acid is a compound in which N-acetyl glucosamine and glucuronic acid are alternately bonded in the shape of a chain. Hyaluronic acid is present in the hyaline body of the eye or the umbilical cord, and has great viscosity and plays an important role in preventing bacterial invasion or poison penetration. This is similar to pectic substance of the plant, and is hydrolyzed by hyaluronidase. Hyaluronic acid was obtained from hyaloids of the bovine eyeballs in 1934 by Meyer, and named as the meaning of uronic acid of the hyaloids. In order to give amphiphilicity and increase solubility in the organic acid, pyridine and acetic anhydride are combined with each other in formamide.

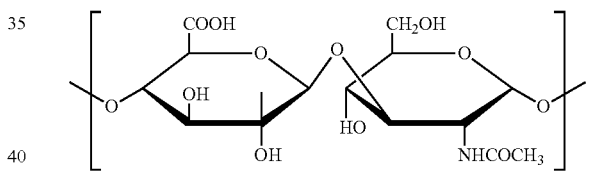

<Structural Formula of Hyaluronic Acid>

In addition, polysaccharide usable in the present invention, chondroitin sulfate, is composed of N-acetylgalactosamine known as a main component of the cartilage, uronic acid (glucuronic acid or iduronic acid), and sulfuric acid, and is also contained in various connective tissues such as skin, umbilical cord, proud flesh, and the like.

Chondroitin sulfate is classified into types A, B, C, D, E, and the like, depending on the kind of uronic acid and the bonding position of a sulfate group.

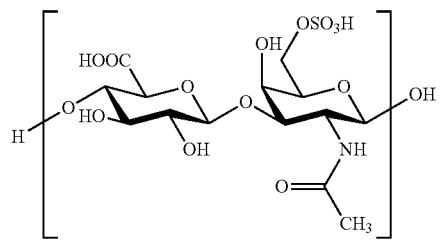

<Structural Formula of Chondroitin Sulfate>

The polymer according to the present invention may be purchased from the market, or isolated and purified from the nature by the method known in the art. Preferably, impurities present in the polymer material may be removed and the polymer may be clearly purified in order to increase purity.

In addition, the acetylation may be performed by dissolving the polysaccharide, that is, the polymer in the organic solvent, and then adding pyridine and acetate anhydride to the solution. The acetylation may be performed by dissolving chondroitin sulfate in the formamide solvent and then adding pyridine and acetate anhydride thereto, followed by stirring for 10~14 hours at a temperature higher than room temperature.

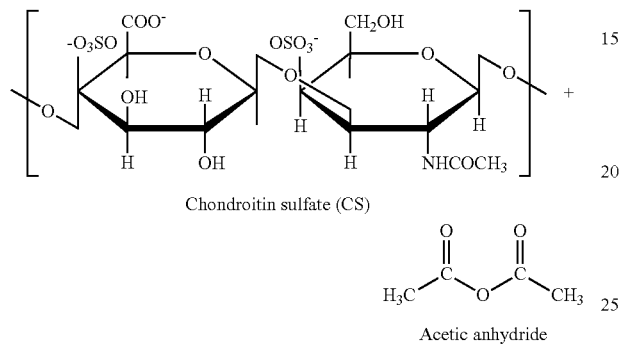

Chondroitin sulfate (CS)

Acetic anhydride

<Acetylation of Chondroitin Sulfate>

Second Step: Dissolving Acetylated Biocompatible Polysaccharide in Organic Solvent In the procedure where the acetylated polysaccharide is dissolved in an organic solvent, an appropriate amount of organic solvent is preferably used so that the polysaccharide can be sufficiently dissolved in the organic solvent. Here, if the use amount of organic solvent is too large, a subsequent removal process through dialysis may be problematic depending on the kind of solvent, such as DMSO or formamide. Whereas, if the use amount of organic solvent is too small, polymers may congeal.

Examples of the organic solvent usable in the present invention may be, but not limited thereto, DMSO, formamide, and DMF, and DMSO or formamide.

Third Step: Binding Photosensitizer to Acetylated Biocompatible Polymer

After the acetylated biocompatible polysaccharide (that is, polymer) is dissolved in the organic solvent through the second step, a phthalocyanine-based compound and a catalyst are added thereto, to thereby bind the phthalocyanine-based compound to the biocompatible polysaccharide.

The binding of the phthalocyanine-based compound and the biocompatible polysaccharide forms an ester bond or an amide bond, according to which the binding of the phthalocyanine-based compound and the biocompatible polysaccharide may be cut by action of the enzyme when the conjugate accumulates in the cancer cell. The ester bond may be formed by binding —$CH_2OH$ group of the biocompatible polymer and —COOH group introduced to the phthalocyanine-based compound to each other.

As the phthalocyanine-based compound in the present invention, one that exhibits fluorescence in the presence of near infrared light, has hydrophobicity, and includes —COOH group as a carboxylated compound may be used. The kind thereof is not limited so long as the compound reacts in the near infrared range and is a phthalocyanine based compound having a —COOH reactive group.

According to some embodiments of the present invention, the phthalocyanine-based compound may be phthalocyanine, a derivative thereof, naphthalocyanine, or a derivative thereof, which contains a metal ion at the center of a structure thereof. Here, the central metal ion may be Zn, Cu, Al, Ga, Co, Fe, Ni, P, or Cr.

More specifically, the phthalocyanine-based compound according to the present invention may be a compound of Chemical Formula 1 below.

[Chemical Formula 1]

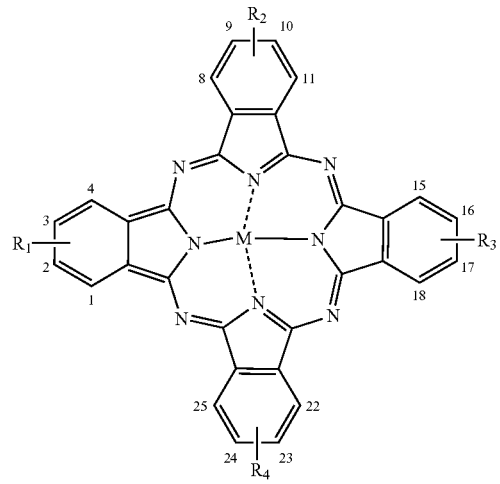

Here, $R_1$, $R_2$, $R_3$ to $R_4$ each may be independently hydrogen, halogen, $C_1$-$C_{10}$ alkyl, —COOH, —$SO_3H$, or a benzene ring substituted or unsubstituted with —COOH, —$SO_3H$, and M may be Zn, Cu, Al, Ga, Co, Fe, Ni, P, or Cr.

In an example of the present invention, a phthalocyanine-based compound represented by Chemical Formula 1-1 below may be used.

[Chemical Formula 1-1]

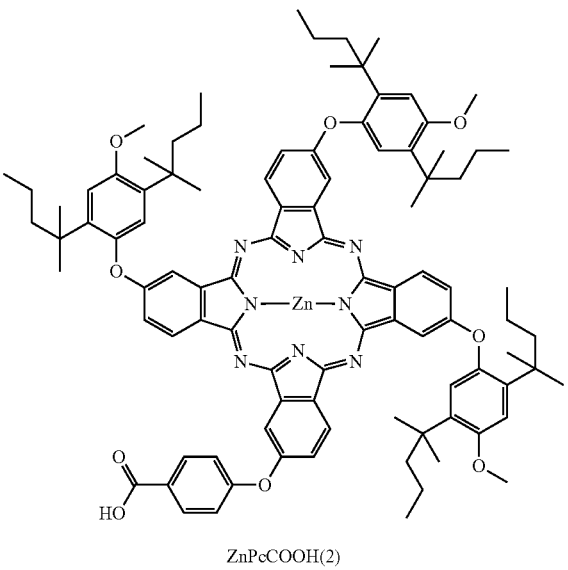

ZnPcCOOH(2)

The phthalocyanine-based compound of Chemical Formula 1-1 used in an example of the present invention is material usable as a superior photodynamic therapeutic agent in that it has higher molar absorptivity in the near infrared wavelength of 600~800 nm than the existing photosensitizer, and thus has a deep penetration depth into an inside of the target cancer, and a desired effect is obtained due to high molar absorptivity event through the input of a small amount thereof.

At the time of a binding reaction, the catalyst is a material that serves to activate —COOH group of the phthalocyanine-based compound, and is used by being dissolved in the organic solvent such as DMSO, formamide, or the like, together with the phthalocyanine-based compound. Examples of the catalyst may be 4-dimethylaminopyridine (DMAP) or 1,3-dicyclohexyl carbodiimide (DCC).

In addition, since the binding reaction of the phthalocyanine-based compound to the biocompatible polysaccharide via an ester bond is carried out by reacting polysaccharide having a relatively large molecular weight with a catalyst and a phthalocyanine-based compound, which have a relatively small molecular weight, the reaction is allowed to proceed while a mixture solution of the phthalocyanine-based compound dissolved in the organic solvent and the catalyst is put into the biocompatible polysaccharide drop by drop, so that the ester bond between the polymer and the photosensitizer can be sufficiently formed. In addition, the reaction may be allowed to proceed while the reactant materials are well stirred in the moistureless and lightless environment for about 45~50 hours for good synthesis.

As set forth above, the conjugate for photodynamic diagnosis or therapy of the present invention, in which the phthalocyanine-based compound is bound to the biocompatible polysaccharide, may be prepared by the foregoing reaction procedure.

Here, the organic solvent used in the binding procedure may be preferably removed. The organic solvent may be removed by a filtration or dialysis method conventionally employed in the art. Preferably, the organic solvent may be removed by using a dialysis membrane.

When the organic solvent is removed through the dialysis membrane, it is to be noted that the ambient temperature is not too high and the temperature is maintained at room temperature at the time of a dialysis procedure since the dialysis membrane is vulnerable to heat. More specifically, since the dialysis membrane may be easily damaged by the heat generated when DMSO or formamide and water encounter with each other, a little water is put into a container after the reaction, to thereby cool the container, before the reacted liquid is put into the dialysis membrane. After that, the reacted liquid is put into the dialysis membrane, which is then put in a water bath, and here it is preferable to change the distilled water until the organic solvent is completely removed.

In addition, the reaction solution subjected to the dialysis procedure may be freeze-dried. The conjugate in which the phthalocyanine-based compound is bound to the biocompatible polysaccharide may be easily collected by the freeze-drying. Any freeze-drying method that is known in the art may be employed, and preferably, freeze-drying may be carried out by using liquid nitrogen. The reaction solution is completely frozen in the liquid nitrogen for about 5 minutes to 15 minutes, and then moisture is completely evaporated by using a vacuum dryer, to thereby collect a desired conjugate.

After that, the conjugate obtained through the freeze-drying is again dissolved in the organic solvent such as DMSO, formamide, or the like, and then subjected to the removing of solvent by dialysis and the freeze-drying in order to remove an unreacted material. These steps are repeated to collect the conjugate, so that purity of the collected conjugate is increased.

In an example of the present invention, the conjugate of the biocompatible polymer and photosensitizer for photodynamic diagnosis was prepared by acetylating chondroitin sulfate as the biocompatible polysaccharide through the addition of pyridine and acetate anhydride thereto and then binding the phthalocyanine-based compound as the photosensitizer to the acetylated polysaccharide. The preparing procedure is shown in the following schematic diagram.

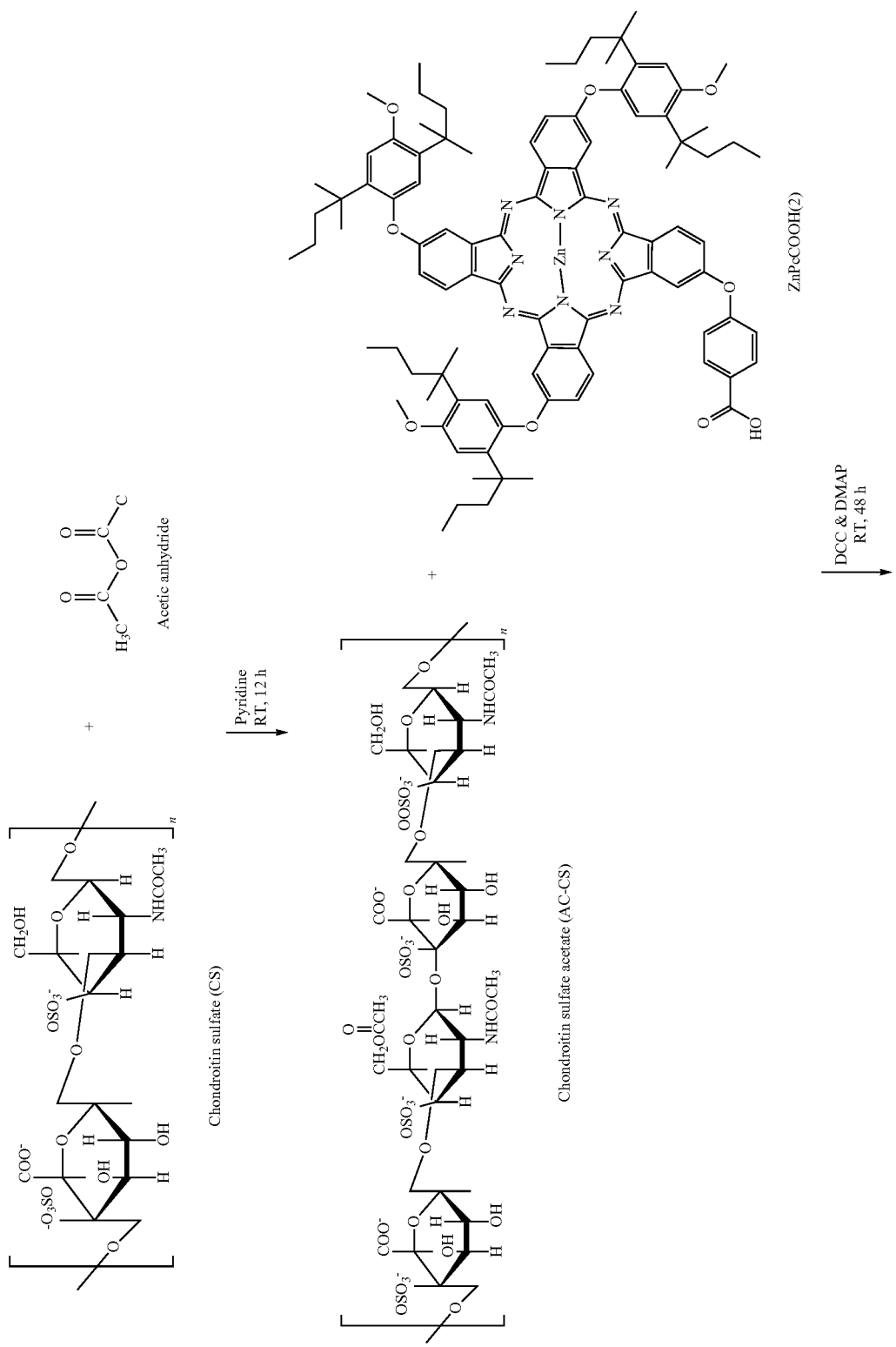

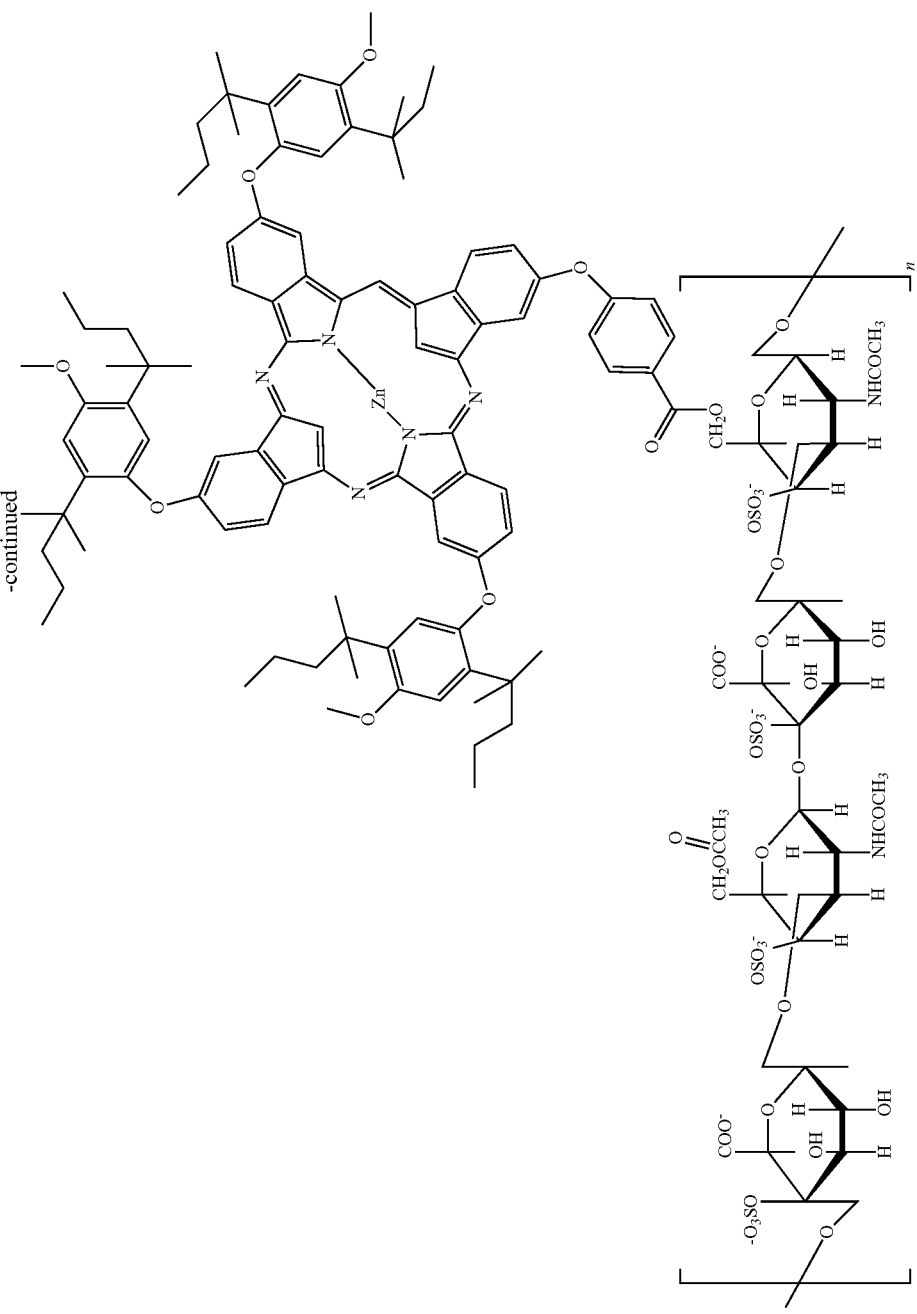

Therefore, the present invention may provide a method for preparing a conjugate of acetylated polysaccharide and phthalocyanine-based compound for photodynamic diagnosis or therapy, and more specifically, the method may comprise: acetylating biocompatible polysaccharide; dissolving the biocompatible polysaccharide in an organic solvent; and adding a phthalocyanine-based compound dissolved in an organic solvent and a catalyst to the biocompatible polysaccharide, to bind the polysaccharide to the phthalocyanine-based compound.

The conjugate for photodynamic diagnosis or therapy of the present invention, which is prepared by the foregoing method, may be in the form of nanoparticle, that is, nano-gel or nano-microsphere, which is stable in a water system, and an average particle size thereof may be 100~250 nm.

According to an example of the present invention, in the procedure for preparing the conjugate, the conjugates are prepared by different concentrations of phthalocyanine-based compound having hydrophobicity and then sizes and shapes of the respective conjugates are measured by using a dynamic light scattering device and an electron microscope. The result shows that, the more the amount of phthalocyanine-based compound is used, the more the hydrophobicity is increased, and thus the cohesive strength is increased, resulting in decreasing the size of the conjugate (nano-microsphere).

Meanwhile, the photosensitizer for photodynamic diagnosis or therapy used in the related art has low accumulation ratio and target ratio with respect to cancer cells and does not induce fluorescent interference, and thus exhibits cytotoxicity in general cells, that is, normal cells in vivo when the light is irradiated, resulting in degrading therapy effects and causing several side effects.

However, the conjugate for photodynamic diagnosis or therapy according to the present invention does not exhibit cytotoxicity at the time of blood circulation or in normal cells even when near infrared ray is irradiated, but the conjugate selectively targets cancer tissues or cancer cells, and accumulates and is decomposed in only cancer tissues or cancer cells, and thus generates singlet oxygen or free radical when near infrared light is irradiated, to exhibit cytotoxicity, resulting in inducing apoptosis in the cancer tissues, so that efficiency of photodynamic therapy can be maximized.

Furthermore, the conjugate for photodynamic diagnosis or therapy of the present invention may further include a cancer cell targeting material in order to selectively target cancer tissues or cancer cells. In the photodynamic therapy, when only the hydrophobic photosensitizer is intravenously injected, it binds to protein in the blood, and moves into the cell through the receptor positioned on a surface of the cell. This is not preferable since specificity of the photosensitizer in cell selection is simply defined by only hydrophobic property of the photosensitizer, and also the residence time thereof in the cell or tissue shows a large difference according to circumstances. In addition, this has been picked as a factor in reducing the effect of photodynamic therapy and increasing the probability of reoccurrence after the therapy.

In order to overcome these problems, the reality is that whether or not the photosensitizer selectively acts on specific regions depends on only the selection method by trial and error simply using various kinds of photosensitizers. However, when the cancer cell targeting material is further bound to the photosensitize in order to effectively and tissue-specifically transfer the photosensitizer, selectivity to the cancer cell can be further improved. The cancer cell targeting material can effectively target and permeate into the cancer cells other than normal cells since a large quantity of specific receptors are exhibited on the surface of the cancer cell.

The cancer cell targeting material in the present invention can bind to the specific receptors of the cancer cell, and examples of the cancer cell targeting material may be folic acid, or a monoclonal antibody against CD133, CD44, CD34, or Bcl-2 protein.

In addition, the conjugate for photodynamic diagnosis or therapy of the present invention has singlet oxygen or free radical formation potential that may induce cytotoxicity at the time of laser irradiation. According to an example of the present invention, it was shown that the conjugate prepared in the present invention, that is, the nano-microsphere, had a similar degree of singlet oxygen formation potential as compared with the phthalocyanine-based compound used as a positive control group.

According to another example of the present invention, an experiment was conducted to confirm whether or not the conjugate for photodynamic diagnosis or therapy of the present invention that does not accumulate in the cancer cell exhibits cytotoxicity in the cell. It was shown that the conjugate assumed in the form of nano-microsphere to induce fluorescent interference in the water system having conditions similar to those in the body, and thus had no reactivity even when near infrared wavelength light was irradiated. Whereas, it was shown that, when the conjugate accumulated in the cancer cell, the conjugate exhibited cytotoxicity and thus increased apoptosis of cancer cells.

Therefore, the present inventors could find from the above results that, when the conjugate of the present invention does not accumulate in the cancer cell, it had no reactivity even where the light is irradiated, and thus does not exhibit cytotoxicity and thus is stale in vivo, and only when the conjugate accumulates in the cancer cell, it exhibits cytotoxicity and thus shows therapy effects.

In addition, when the conjugate of the present invention selectively targets and permeates into the cancer cell, the ester bond is cut (decomposed) by an enzyme action of the cancer cell, that is, an enzyme such as esterase, which is an in vivo enzyme, so that the fluorescent interference is released, resulting in exhibiting fluorescence.

Therefore, according to the present invention, when the conjugate of the present invention selectively accumulates in the cancer tissue or the cancer cell, the fluorescent interference may be released by an enzyme action in the cancer cell and the phthalocyanine photosensitizer may exhibit fluorescence in only the cancer cell by laser irradiation, so that the cancer diagnosis can be made by the presence or absence of fluorescence.

Further, the present invention may provide a composition for cancer therapy, containing the conjugate as an effective component.

The term 'therapy' herein, unless stated otherwise, means reversing, mitigating, suppressing the progress of, or preventing disease, illness, or one or more symptoms of the disease or illness to which the term is applied.

The composition for cancer therapy according to the present invention may comprise a pharmaceutically effective amount of the conjugate for photodynamic diagnosis or therapy of the present invention alone, or may further comprise at least one pharmaceutically acceptable additive such as, carrier, vehicle, diluent, or the like. The term pharmaceutically effective amount means an amount sufficient to prevent, improve, and treat symptoms of the cancer.

The pharmaceutically effective amount of the conjugate for photodynamic diagnosis or therapy according to the present invention is 0.5~100 mg/day/kg body mass, and preferably 0.5~5 mg/day/kg body mass. However, the pharmaceutically effective amount may be appropriately varied depending on the severity of the symptom, age, weight, health status, and gender of the patient, route of administration, duration of treatment, and the like.

Herein, the term pharmaceutically acceptable additive means one that is physiologically acceptable and does not cause gastrointestinal disorders, allergic reactions such as dizziness, or similar reactions when being administered to a human. Examples of the carrier, vehicle, and diluent may be lactose, dextrose, sucrose, sorbitol, mannitol, xylitol, erythritol, maltitol, starch, acacia rubber, alginate, gelatin, calcium phosphate, calcium silicate, cellulose, methyl cellulose, polyvinyl pyrrolidone, water, methylhydroxy benzoate, propylhydroxy benzoate, talc, magnesium stearate, and mineral oil. In addition, they may further comprise filler, anti-coagulant, lubricant, wetting agent, flavoring, emulsifier, and preservative.

In addition, the composition of the present invention may be formulated by using the method known in the art so that an active component is provided in a manner of fast release, sustained release, or delayed release after the composition is administered to a mammal. The dosage form may be powder, granule, tablet, emulsion, syrup, aerosol, soft or hard gelatin capsule, sterile injectable solution, or sterile powder.

The composition for cancer therapy according to the present invention may be administered through several routes including oral, transdermal, subcutaneous, intravenous, and muscular routes, and the dosage of the active component may be appropriately selected depending on several factors such as route of administration, and age, gender, weight, and severity of symptom, of the patient.

In addition, in the case where the conjugate according to the present invention or the composition including the conjugate is used to conduct therapy or diagnosis of diseases, a light source usable in the present invention may be, but is not limited thereto, at least one selected from the group consisting of light sources for in vitro light irradiation including an ultrasonic irradiation emitter, a light emitting diode, a laser diode, a dye laser, a halogenated metal lamp, a flash lamp, a mechanically filtered fluorescent light source, a mechanically filtered incandescence, a filament light source, and the like; and light sources for in vivo light irradiation including a laser fiber for photodynamic therapy and the like. In the present invention, the photosensitizer may exhibit activity in the near infrared ray in the range of 600 nm to 700 nm.

In addition, since the conjugate according to the present invention contains hydrophilic polysaccharide and hydrophobic phthalocyanine-based compound, the conjugate assumes in the form of a nano-microsphere. The nano-microsphere may further include medicine or a biological agent having therapeutic activity, and preferably include an anti-cancer agent. Here, the medicine or biological agent may be included while being sealed inside the nano-microsphere.

Hereinafter, the present invention will be described in more detail with reference to examples. These examples are only for specifically explaining the present invention, and it will be obvious to those skilled in the art that the scope of the present invention is not limited to these examples.

Example 1

Preparation of Nano-Microsphere for Photodynamic Diagnosis or Therapy

<1-1> Preparation of Phthalocyanine-based Compound

<1-1-1> Synthesis of Precursor R1

4-methoxy-3,6-tert-butylphenol 3.66 g (15.6 mmol) and 4-nitrophthalonitrile 2.70 g (15.6 mmol) were added to 100 ml of DMSO and purged with $N_2$, and then the temperature was raised to the temperature for reflux. $K_2CO_3$ 2.86 g was put thereinto from the start of reflux to 4 hours, which was then maintained for 24 hours.

After reflux for 24 hours, 100 ml of water was added thereto, followed by stirring, and then $K_2CO_3$ and DMSO were removed to precipitate a white material having slight viscosity. Sufficient ether was added thereto to extract only the product, which was then dried by using an evaporator, to thereby obtain Product 1-1-1 having pale yellow.

<1-1-2> Synthesis of COOH Precursor R2

Pentyl-4-hydroxybenzoate 2.405 g (12.37 mmol) and 4-nitrophthalonitrile 2 g (11.56 mmol) were added to 82.5 ml of anhydrous DMSO and purged with $N_2$, and then the temperature was raised to the temperature for reflux. $K_2CO_3$ 1.054 g was put thereinto every hour from the start of reflux to 4 hours, which was then maintained for 29 hours, and then it was confirmed that 4-nitrophthalonitrile was absent through TLC chromatography.

After reflux for 29 hours, drying with an evaporator was conducted to obtain a dark brown product. Sufficient amounts of EA and water were added thereto, to dissolve the entire product, followed by extraction. The separated water layer was subjected to repetitive several times of extraction with EA, and the thus obtained solution was dried by using an evaporator until the solution reaches about only 150 ml, and then washed with 200 ml of saturated aqueous $NaHCO_3$ solution. After stirring well in a separatory funnel, the EA layer was obtained by being passed through $MgSO_4$, and then again dried by an evaporator, to obtain a dark brown liquid phase product, and also about 1 g of Product 1-1-2 in a liquid phase, which is a material purely separated through column purification, was obtained.

<1-1-3> Synthesis of Phthalocyanine Derivative

The prepared Product 1-1-2, benzoate precursor 0.334 g and Product 1-1-1, alkyl precursor 0.837 g were added to 50 ml of anhydrous pentanol, and then $ZnCl_2$ 0.409 g was added thereto. Then, Ar gas was sufficiently introduced thereinto. The reaction liquid was temperature-raised to 150° C., followed by dropping 2.25 ml of DBU, and then the reflux was allowed to proceed for 24 hours. After 24 hours, evaporation was allowed to proceed, to obtain a dark blue-green product. The obtained product was purified by column chromatography with MC and MeOH, to obtain a blue-green solid material 1-1-3.

Figure 3:
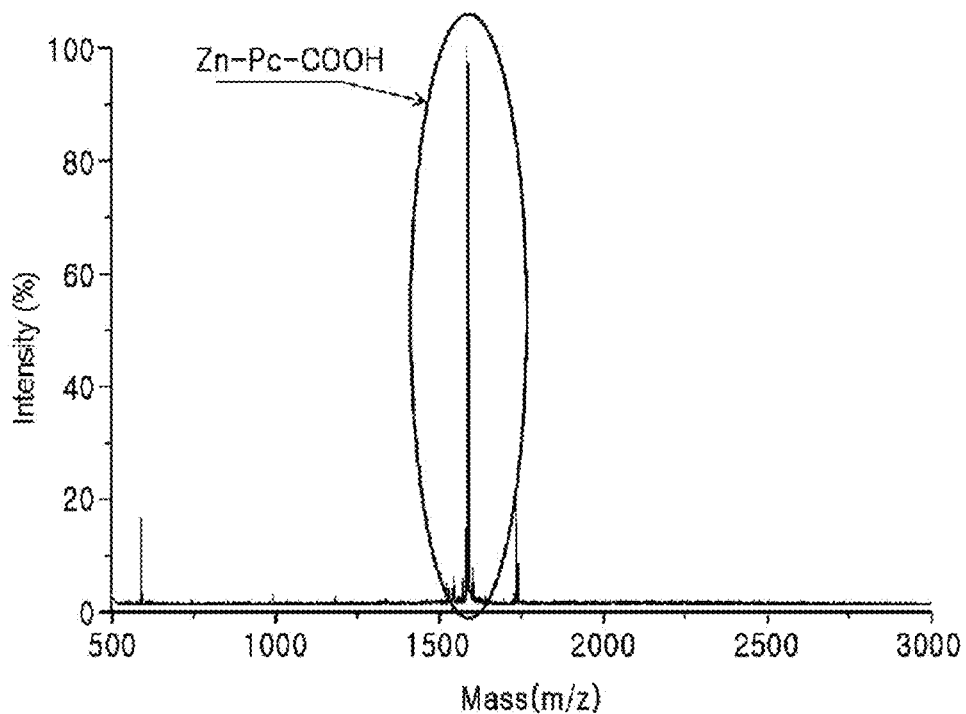
FIG. 3 is a graph showing Maldi-TOF analysis results of a phthalocyanine-based compound used in examples of the present invention.

The thus obtained material 1-1-3 was dissolved in 40 ml of THF, and then mixed with a solution in which $LiOH.H_2O$ (1 g. 23.34 mmol) was dissolved in 7:3 of methanol and $H_2O$, and the temperature was raised to 75° C., followed by reflux for 17 hours. After reflux for 17 hours, the solution was evaporated. The residual was dissolved in about 100 ml of MC, and was titrated to pH 2 while an aqueous 0.1M HCl solution was added dropwise thereto, followed by stirring at room temperature for 3 hours. After that, extraction was conducted (MgSO$_4$ pass) with sufficient water, followed by column chromatography with CHCl$_2$ and MeOH. The molecular weight of the final product was confirmed by Maldi-TOF, and the results thereof are shown in FIG. 3.

Phthalocyanine-based compound having Chemical Formula 1-1 below was obtained through the above example.

[Chemical Formula 1-1]

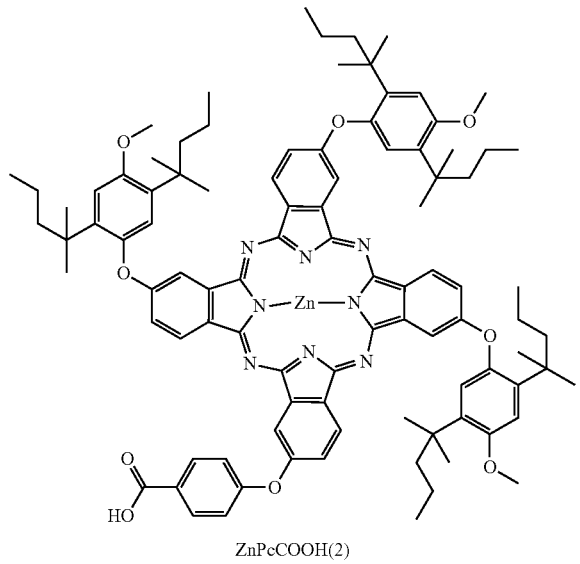

ZnPcCOOH(2)

<1-2> Acetylation of Chondroitin Sulfate

Chondroitin Sulfate (0.5 g) was dissolved in 10 ml of a formamide solvent. After that, 55 μl of pyridine and 55 μl of anhydrous acetate were added thereto, and then the reaction was allowed to proceed while well stirring for about 12 hours at 55° C., which is somewhat high. The thus obtained sample after the reaction was collected by dialysis through a dialysis membrane and then freeze-drying.

<1-3> Binding of Acetylated Chondroitin Sulfate and Photosensitizer 50 mg of the acetylated chondroitin sulfate that was collected by freeze-drying in the <1-2> was dissolved in 10 ml of a dehydrated organic solvent, DMSO or formamide, respectively. Meanwhile, 1 mg, 2 mg, and 5 mg of the phthalocyanine-based compound as a photosensitizer, which was prepared in <1-1>, were sufficiently dissolved in 3 ml of DMSO or formamide, together with DMAP and DCC, respectively, to activate —COOH group. 3 ml of each of the photosensitizer solutions having activated —COOH groups was put into 10 ml of the organic solvent in which the acetylated chondroitin sulfate was dissolved, and then an ester binding reaction was allowed to sufficiently proceed for about 48 hours while stirring well. The solution after the reaction was completed was collected by the same procedure as Example <1-2>, and then kept in a freezer, so that the conjugate for photodynamic diagnosis or therapy according to the present invention, that is, a nano-microsphere, was prepared, and respective samples were called Ac—Cs—Zn-Pc-COOH1, Ac—Cs—Zn-Pc-COOH2, Ac—Cs—Zn-Pc-COOH3, respectively.

Figure 4:
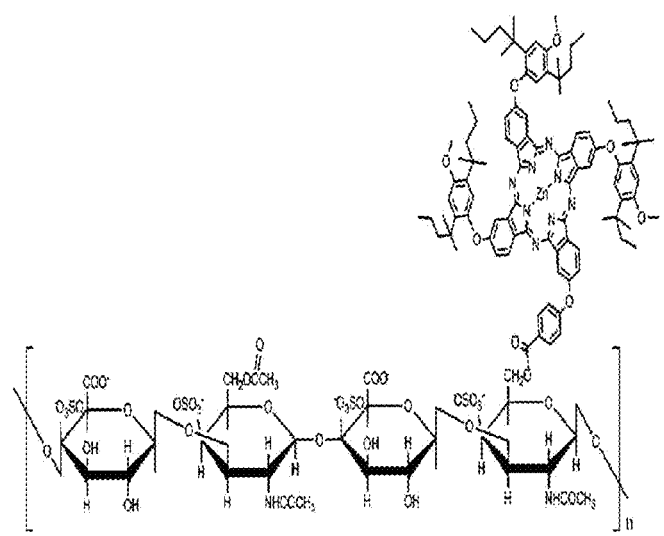
FIG. 4 is a schematic view showing a structural formula of the conjugate, Ac—Cs—Zn-Pc-COOH, in which a phthalocyanine-based compound is bound to chondroitin sulfate via an ester bond.
Figure 5:
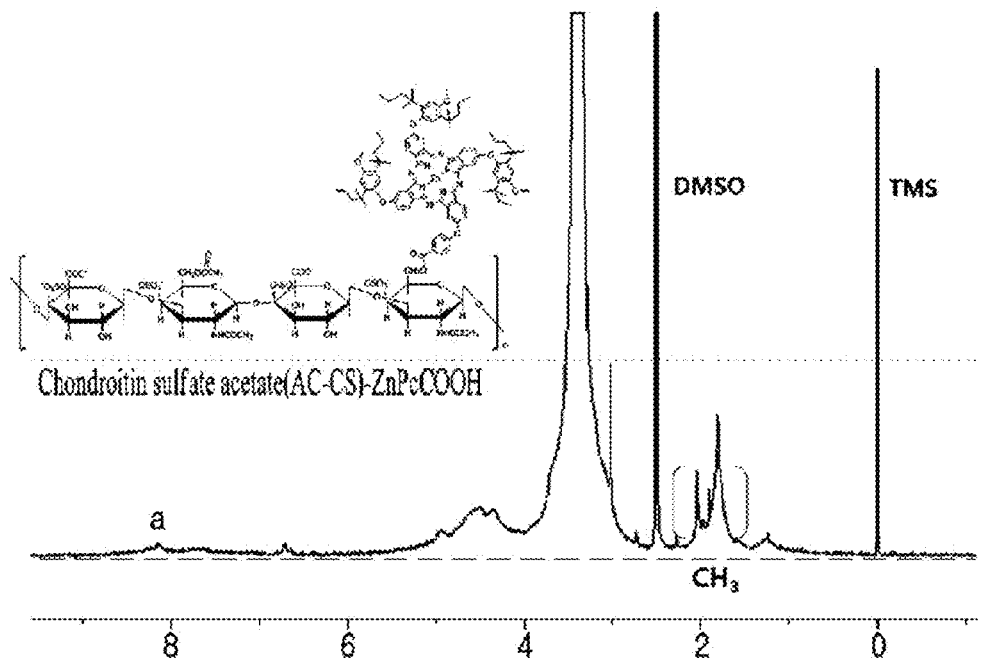
FIG. 5 shows NMR analysis results of Ac—Cs—Zn-Pc-COOH.
Figure 6:
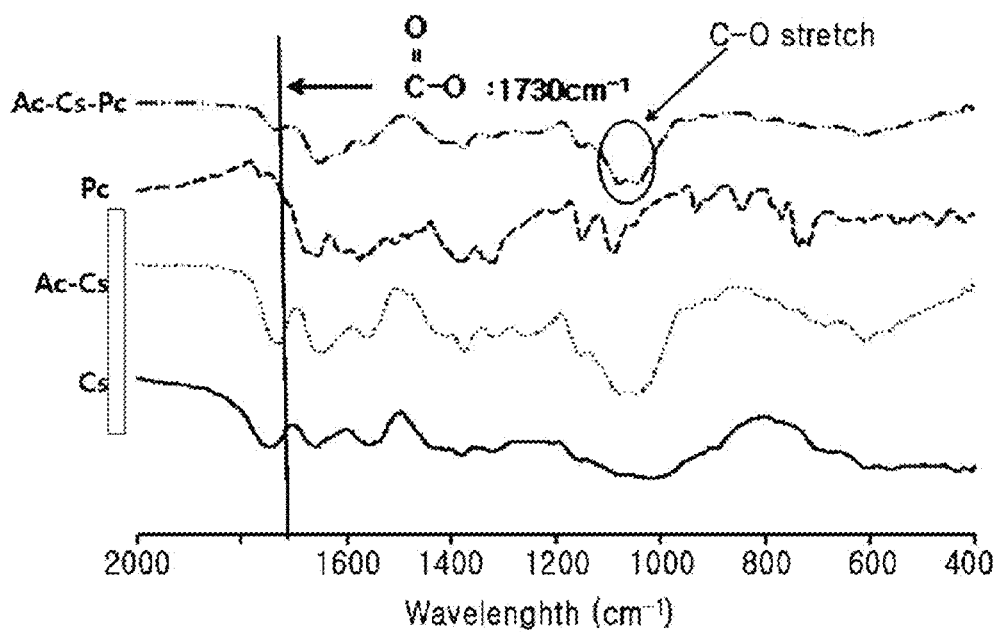
FIG. 6 shows FT-IR analysis results of Ac—Cs—Zn-Pc-COOH.
Figure 7:
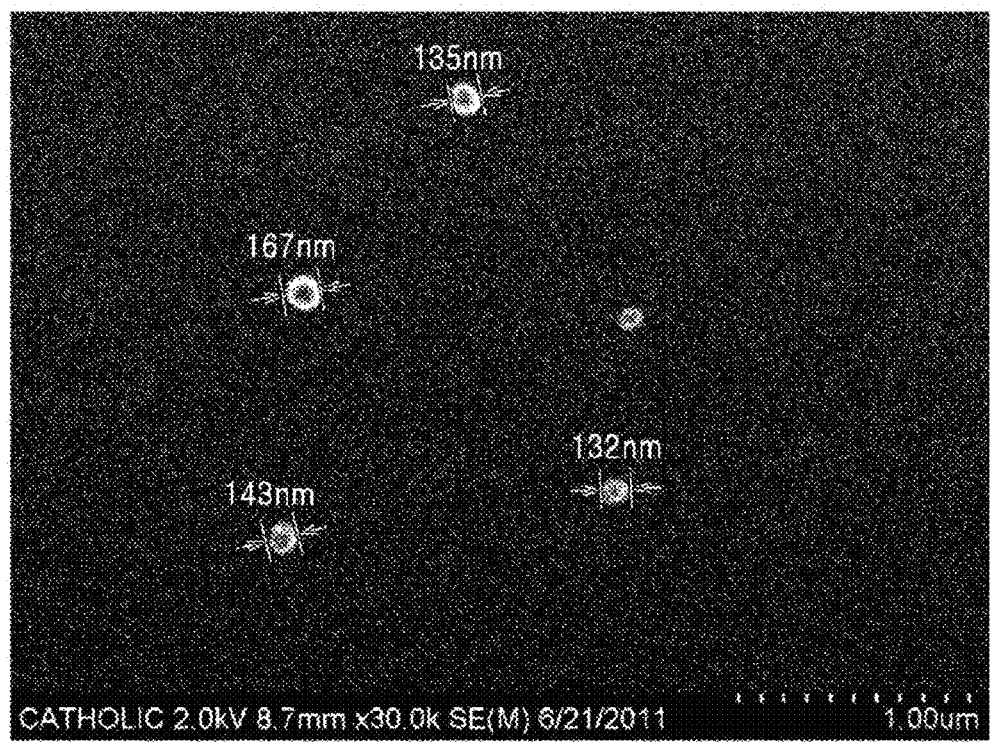
FIGS. 7 to 11 show results measured by using a dynamic light scattering device and an electron microscope a conjugate (nano-microspheres) for photodynamic diagnosis or therapy prepared according to an example of the present invention, and in particular show observation results of the size distribution and shape when Ac—Cs—Zn-Pc-COOH prepared from Example 1 of the present invention assumes in the form of nano-microspheres.
Figure 8:
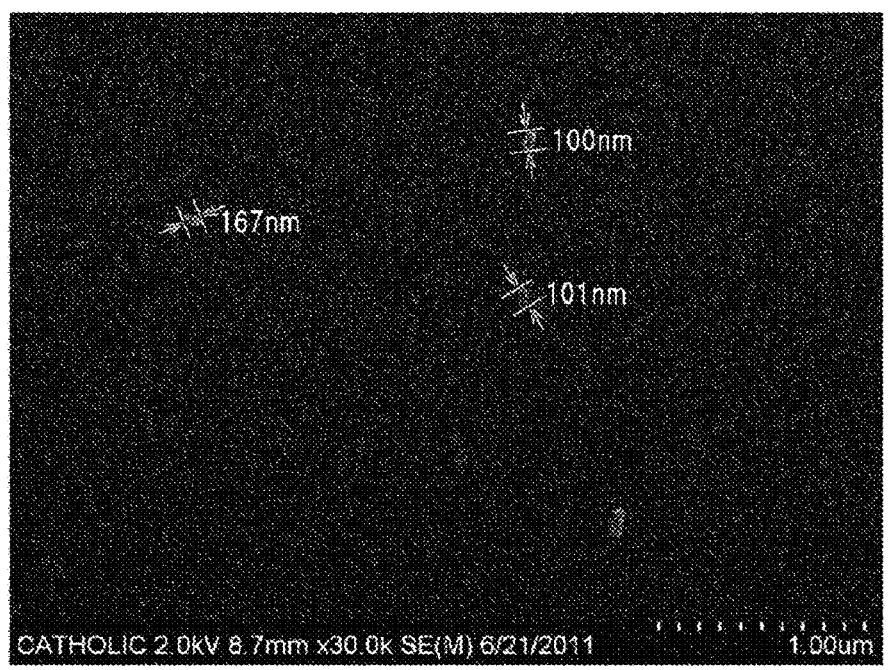

FIG. 4 is a schematic view showing a structural formula of the conjugate, Ac—Cs—Zn-Pc-COOH, in which chondroitin sulfate and phthalocyanine-based compound of Chemical Formula 1-1 are bound to each other via an ester bond. Also, as for FT-IR analysis results of Ac—Cs—Zn-Pc-COOH as shown in FIG. 6, Ac—Cs—Zn-Pc-COOH data confirmed the peak at 1730 cm$^{-1}$ representing the ester bond, which is a binding characteristic between biocompatible polymer and phthalocyanine-based compound.

Example 2

Characteristic Analysis of Nano-Microsphere

<2-1> Measurement of Size and Shape of Nano-Microsphere

Figure 9:
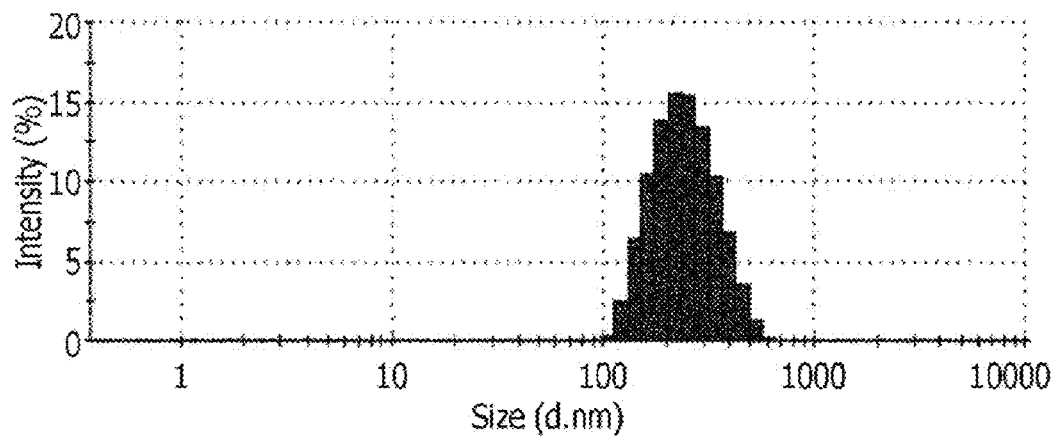
Figure 10:
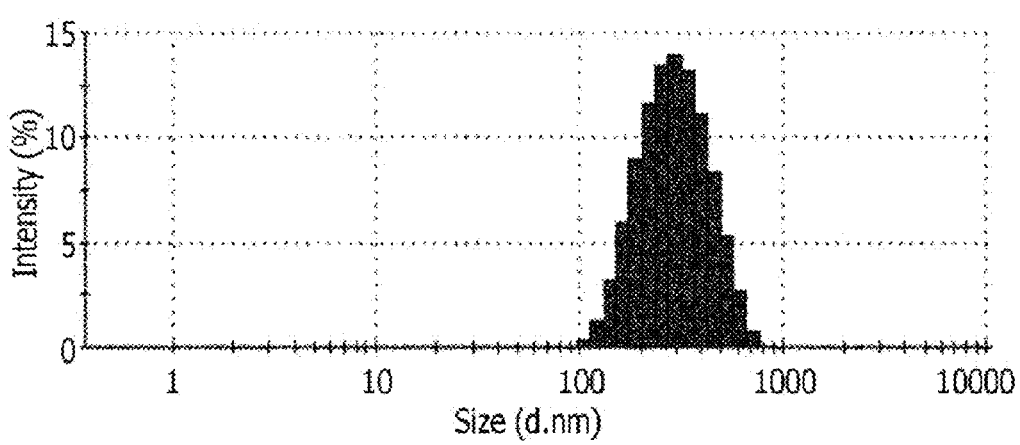
Figure 11:
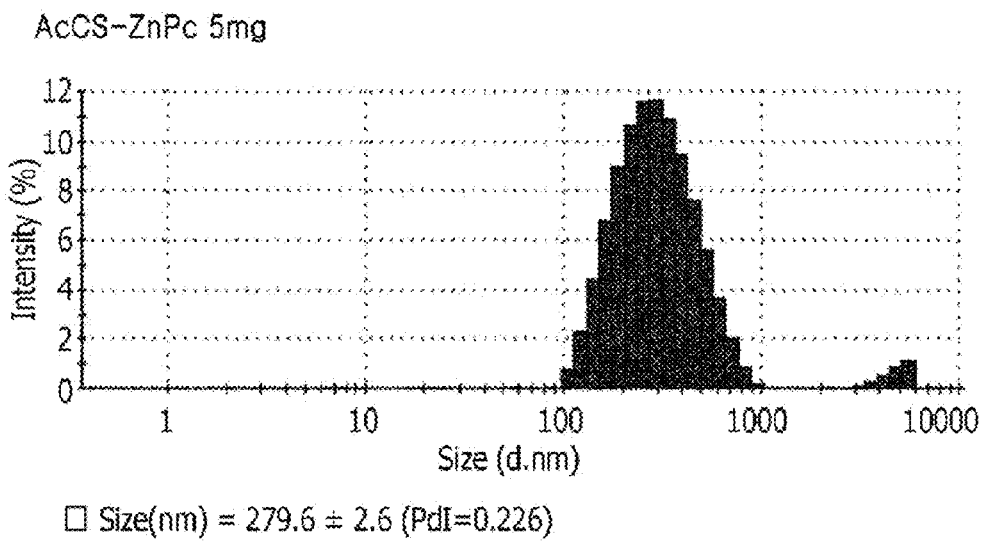

Three biocompatible material samples prepared from Example 1, in which the phthalocyanine-based compound is bound to the acetylated chondroitin sulfate, were dissolved at a concentration of 1 mg/ml, and then the sizes thereof were measured by using the dynamic light scattering (DLS) and the shapes thereof were confirmed by using a field emission scanning electromicroscopy (FE-SEM). Here, for accurate size measurement, the samples were diluted with 0.1M NaCl. The results are shown in FIGS. 7 to 11. It was shown that the sizes and shapes of the nano-microspheres formed by binding the phthalocyanine-based compound to chondroitin sulfate as biocompatible polysaccharide via an ester bond were distributed in the range of 100~800 nm and converged at about 230 nm, as shown in FIGS. 9 to 11. In addition, in 3A, a large particle represents a case for a small amount of photosensitizer (Ac—Cs—Zn—PC—COOH1), and a small particle represents a case for a large amount of photosensitizer (Ac—Cs—Zn—PC—COOH2). Accordingly, it was seen that, the more the amount of photosensitizer is bound to polysaccharide, the more the hydrophobicity of the conjugate is increased and thus the cohesive strength is increased, resulting in decreasing the size of the nano-microsphere.

<2-2> Confirmation on Presence or Absence of Fluorescent Interference

Figure 12:
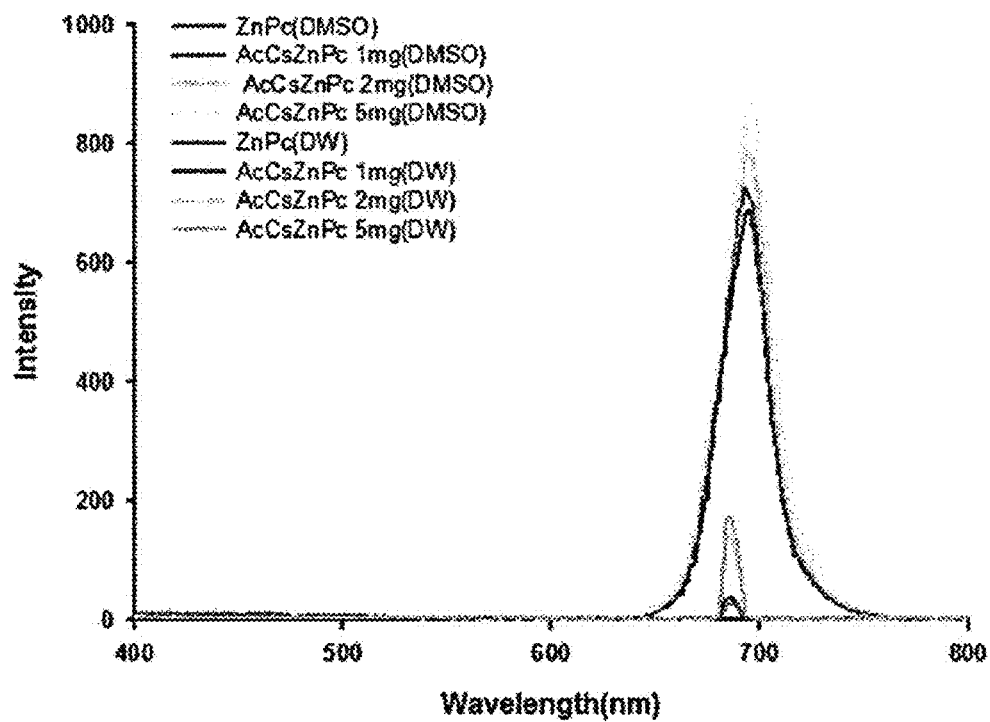
FIG. 12 is a graph for comparing fluorescent intensities between when fluorescent interference effect is shown and when fluorescent interference effect is not shown, for nano-microspheres of the present invention prepared according to an example of the present invention, that is, Ac—Cs—Zn-Pc-COOH prepared from Example 1, and shows by comparing and observing between fluorescent values for several concentrations of Ac—Cs—Zn-Pc-COOH in DMSO and Di-water and fluorescent values for unmodified Zn-Pc-COOH in DMSO and Di-water.

Several concentrations of the obtained Ac—Cs—Zn-Pc-COOH from Example 1 were dissolved in DMSO and Di-water, respectively, and then fluorescent phenomena thereof were confirmed by using the KODAK image station and the fluorescent spectrophotometer (FIG. 12). At the time of measurement in the wavelength range of 650~750 nm, fluorescent intensities and images were shown to be different depending on the concentration for DMSO, that is, organic solvent (A), but self fluorescent interference occurred for Di-water, and thus significantly lower fluorescence as compared with DMSO were exhibited. It is thought that the reason is that Ac—Cs—Zn—COOH does not form a microsphere in the organic solvent and thus does not induce fluorescent interference, but forms a nano-microsphere in Di-water and thus induces fluorescent interference. The present inventors could find from these results that, in the photodynamic therapy, the nano-microsphere that does not accumulate in the cancer cell does not exhibit cytotoxicity, and thus is stably usable in vivo.

<2-3> Evaluation on Singlet Oxygen Formation Potential of Nano-Microsphere

Figure 13:
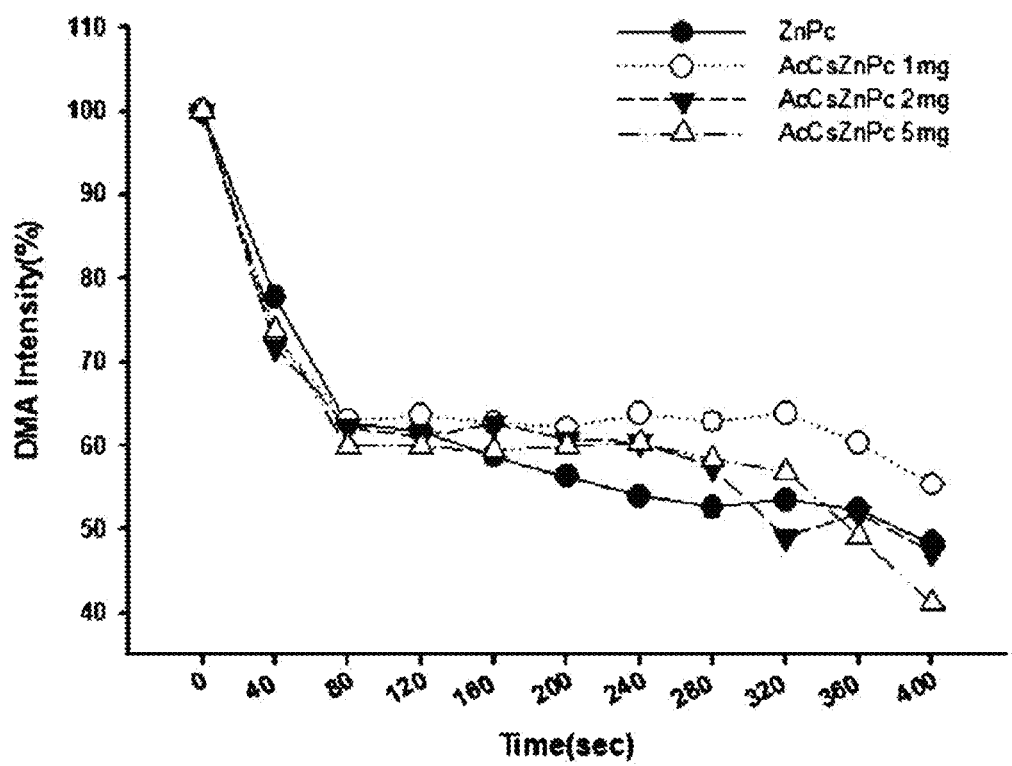
FIG. 13 is a graph showing singlet oxygen formation potential by laser irradiation, for nano-microspheres of the present invention prepared according to an example of the present invention, that is, Ac—Cs—Zn-Pc-COOH prepared from Example 1, wherein ●- represents oxygen formation potential of unmodified Zn-Pc-COOH in DMSO; and -○-, -▼-, and -Δ- represent oxygen formation potentials of 1 mg, 2 mg, and 5 mg of the nano-microspheres according to the present invention in DMSO, respectively.

In order to verify the usability of the conjugate of Example 1, Ac—Cs—Zn-Pc-COOH, as an agent for photodynamic diagnosis or therapy, singlet oxygen formation potential thereof was measured according to the laser irradiation, by being compared with the phthalocyanine based photosensitizer prepared from Example 1-1, which was not modified. First, the conjugate Ac—Cs—Zn-Pc-COOH and the unmodified phthalocyanine photosensitizer were dissolved in 2 ml of DMF and PBS, organic solvents, (phthalocyanine photosensitizer: 1.5 μg/ml), respectively, and then a small amount of 9,10-dimethylanthracene capable of detecting singlet oxygen was put thereinto, to be adjusted to a concentration of 20 μg/ml. Laser irradiation was conducted at a time interval of 40 seconds while using a laser having a wavelength of 670 nm, at which the phthalocyanine photosensitizer has been known to generate singlet oxygen, then fluorescence measurement was conducted mat Ex 360 nm and Em 380~550 nm by using a spectro-fluorephotometer. The above experimental results confirmed that the conjugate of the present invention Ac—Cs—Zn-Pc-COOH could generate singlet oxygen at almost a similar level as compared with the unmodified Zn-Pc-COOH, as shown in FIG. 13. For this reason, it was seen that the nano-microsphere of the present invention could kill the cancer cells by generating singlet oxygen in the target cells (cancer cells).

Figure 14:
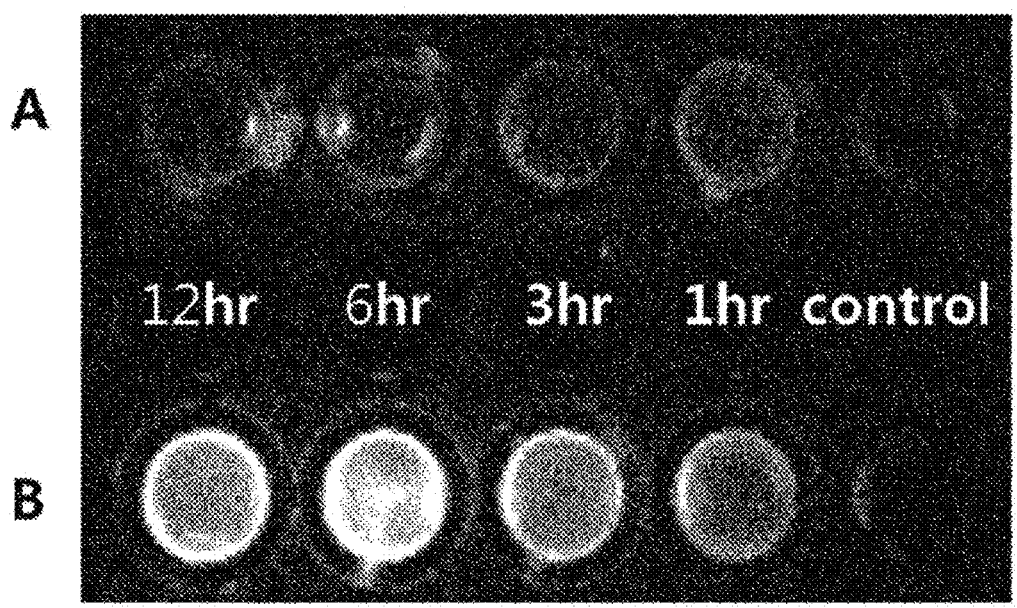
FIG. 14 shows image results showing the degrees of fluorescence exhibited due to decomposition by an enzyme action of cancer cells when IoN of nano-microspheres of the present invention prepared according to an example of the present invention, that is, Ac—Cs—Zn-Pc-COOH prepared from Example 1, was treated with Culture Medium A without cancer cells and Culture Medium B with cancer cells, respectively.

<2-4> Measurement Experiment on Release of Fluorescent Interference by Enzyme Action of Cancer Cell HeLa cells were dispensed at a cell number of $1 \times 10^4$ and then incubated on a 96-well plate. The cells were treated with 10 μg of nano-microspheres of the present invention, and then fluorescent phenomena thereof were observed by using the KODAK image station device. Here, the culture medium without HeLa cells, treated with the nano-microspheres of the present invention was used as a control group. As a result, it was observed that the fluorescent interference was not released for wells containing a general culture medium without HeLa cells, but the fluorescent interference was released to exhibit fluorescence with the lapse of time for wells containing a culture medium to which the HeLa cells are dispensed, as shown in FIG. 14. Therefore, the present inventors could find from the above results that, when the nano-microspheres prepared by the present invention target and accumulate in the cancer cell, the fluorescent interference is released by enzyme action of the cancer cell, and subsequently, when near infrared ray is irradiated, a photosensitizer of the nano-microsphere kills the cancer cell, so that the nano-microsphere of the present invention can treat cancer.

<2-5> Evaluation Experiment on Cytotoxicity

Cytotoxicity test was conducted on the nano-microsphere according to the present invention prepared from Example 1. HeLa cells as cancer cells were incubated in the RPMI 1640 culture medium containing 10% FBS and 1% penicillin in the presence of 5% $CO_2$ at a temperature of 37° C. Then, for the cytotoxicity test, the incubated HeLa cells were dispensed on a 96-well plate at a cell number of $1 \times 10^4$ and then incubated for 24 hours. Next day, the nano-microspheres (nano-microspheres added with 1.25 mg of a photosensitizer) according to the present invention were diluted by concentrations, respectively, and then the diluted concentrations were put into each well at 100 μl.

After that, the cells were further incubated for 12 hours so that the nano-microspheres can act on the cells, and then near infrared wavelength light (670 nm) was irradiated at an amount of 1.2 J/cm². Here, as a control group, a cell group that had the same concentration and treatment time but not subjected to irradiation of the light as compared with the respective samples was used. After that, the cells were incubated in an incubator for one day.

Lastly, 20 μl of MTT reagent (3-(4,5-dimethylthiazol-2yl)-2,5-diphenyl-2H-tetrazolium bromide) was added to the cells after incubation was completed, followed by again incubating for 3~4 hours. After 4 hours, the culture medium, the MTT reagent, and the like, were removed, and then 150 μl of DMSO was added thereto, to dissolve non-soluble formazan exhibiting blue violet, which was formed on the cells. After that, the ELIZA analyzer was used to measure absorbance at 595 nm and thus comparison of the amount of formazan formed was conducted, to thereby confirm cell viability (%) and cytotoxicity of the conjugate (FIGS. 15 and 16).

Figure 15:
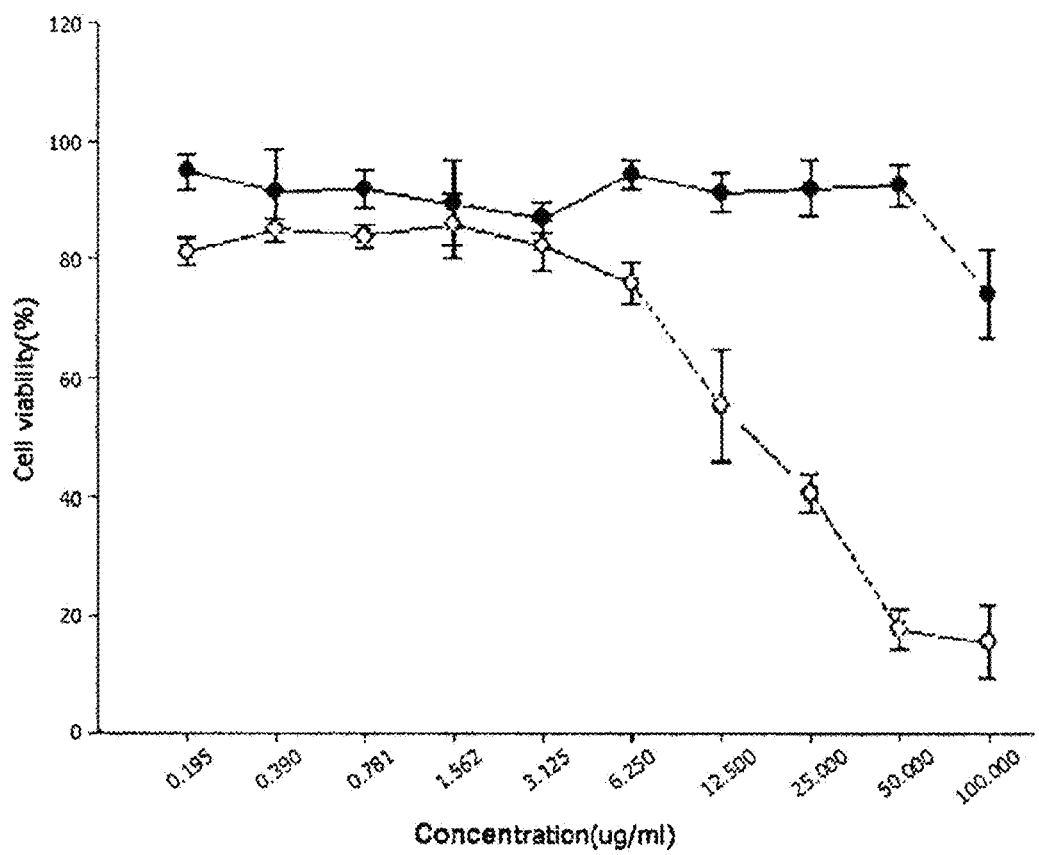
FIGS. 15 and 16 are comparative graphs when nano-microspheres of the present invention prepared according to an example of the present invention, that is, Ac—Cs—Zn-Pc-COOH prepared from Example 1, and unmodified Zn-Pc-COOH used as a control group, were allowed to absorb into cells, followed by laser irradiation, and then apoptosis was observed through an MTT reagent, and the total time for laser irradiation was 8 minutes.
Figure 16:
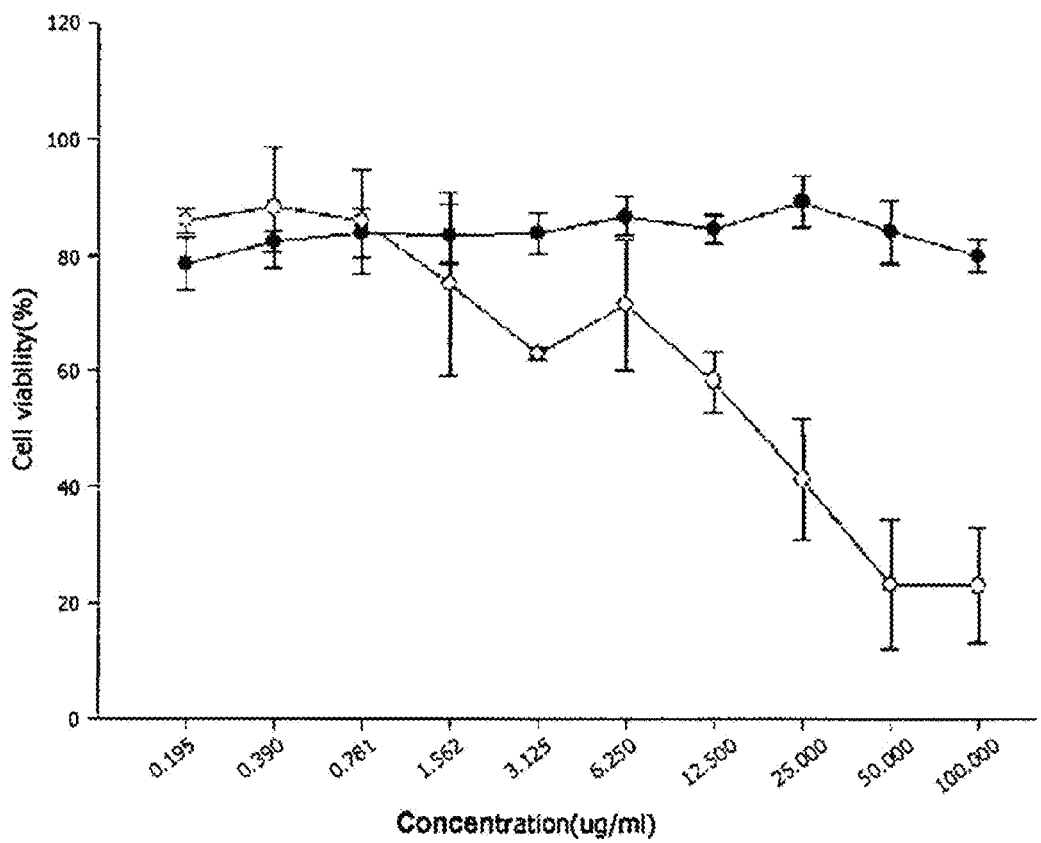

As a result, it may be seen that, as shown in FIGS. 15 and 16, when the unmodified Zn-Pc-COOH and nano-microspheres prepared in the present invention were added to the respective cells, which were then incubated, apoptosis did not occur in the case where near infrared ray was not irradiated, whereas apoptosis occurred in proportional to the time for irradiation in the case where near infrared ray was irradiated, and thus cell viability (%) was decreased. Accordingly, it may be again confirmed that, as shown in the above results, the photosensitizer generates singlet oxygen only when the light is irradiated, and thus kills the cells, and when the nano-microspheres are added to the cells, the fluorescent interference isolated by the polymer is released by the enzyme, to generate singlet oxygen and thus kill the cells.

Hitherto, the present invention was described based on the preferable embodiments.

It will be appreciated by those skilled in the art that various modifications, changes, and substitutions can be made without departing from the essential characteristics of the present invention. Accordingly, the embodiments disclosed in the present invention and the accompanying drawings are used not to limit but to describe the spirit of the present invention. The scope of the present invention is not limited only to the embodiments and the accompanying drawings. The protection scope of the present invention must be analyzed by the appended claims and it should be analyzed that all spirit within a scope equivalent thereto are included in the appended claims of the present invention

INDUSTRIAL APPLICABILITY

The conjugate of the present invention can easily accumulate in the cancer cell in vivo, and the materials of the present invention that do not accumulate cannot exhibit cytotoxicity due to fluorescent interference even when near infrared wavelength light was irradiated. Further, when the conjugate of the present invention accumulates in the cancer cell, the bond between the biocompatible polysaccharide and the photosensitizer is disconnected by the enzyme in the cancer cell, and here, when the near infrared wavelength light is irradiated, the conjugate exhibits cytotoxicity and thus maximizes anti-cancer effects at the time of near infrared irradiation, and also exhibits fluorescence and thus may be used for imaging.

The invention claimed is:

1. A conjugate for photodynamic diagnosis or therapy, in which acetylated biocompatible polysaccharide is bound to a phthalocyanine-based compound of the following Formula 1-1:

[Formula 1-1]

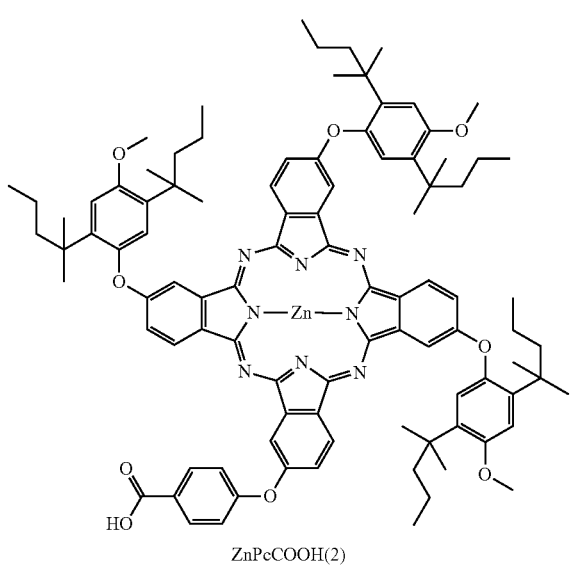

ZnPcCOOH(2)

wherein the conjugate is nanoparticle having 100~250 nm of average particle size and is formed by means of an ester bond of the biocompatible polysaccharide and the phthalocyanine-based compound, and wherein the conjugate is decomposed by an enzyme reaction when the conjugate accumulates in a cancer cell, thereby releasing fluorescent interference such that when near infrared irradiation is applied, the cancer cell is killed.

2. The conjugate for photodynamic diagnosis or therapy of claim 1, wherein the phthalocyanine-based compound exhibits fluorescence in near infrared light.

3. The conjugate for photodynamic diagnosis or therapy of claim 1, wherein the biocompatible polysaccharide is pullulan, hyaluronic acid, dextran, or chondroitin sulfate.

4. The conjugate for photodynamic diagnosis or therapy of claim 1, a cancer cell targeting material is further bound to the biocompatible polysaccharide.

5. The conjugate for photodynamic diagnosis or therapy of claim 4, wherein the cancer cell targeting material is folic acid, or a monoclonal antibody against CD133, CD44, CD34, or Bcl-2 protein.

6. A method for preparing a conjugate for photodynamic diagnosis or therapy, the method comprising the steps of:
acetylating biocompatible polysaccharide; dissolving the acetylated biocompatible polysaccharide in an organic solvent; and adding a phthalocyanine-based compound of the following Formula 1-1 and a catalyst to the biocompatible polysaccharide to bind the photosensitizer to the biocompatible polysaccharide:

[Formula 1-1]

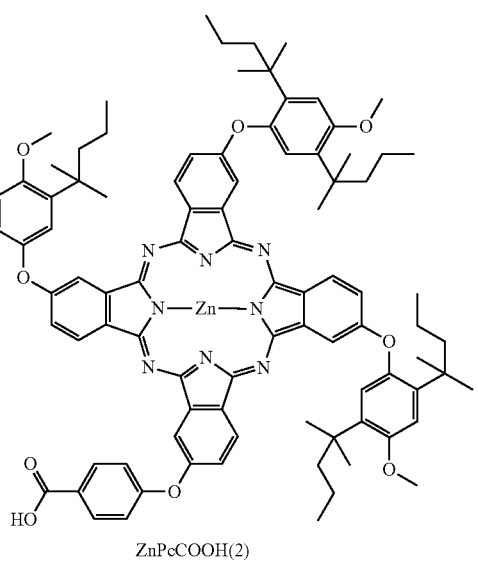

ZnPcCOOH(2)

wherein the conjugate is nanoparticle having 100~250 nm of average particle size and is formed by means of an ester bond of the biocompatible polysaccharide and the phthalocyanine-based compound, and wherein the conjugate is decomposed by an enzyme reaction when the conjugate accumulates in a cancer cell, thereby releasing fluorescent interference such that when near infrared irradiation is applied, the cancer cell is killed.

7. The method for preparing a conjugate for photodynamic diagnosis or therapy of claim 6, wherein the biocompatible polysaccharide is selected from the group consisting of pullulan, hyaluronic acid, dextran and chondroitin sulfate.

8. The method for preparing a conjugate for photodynamic diagnosis or therapy of claim 6, wherein the catalyst is 4-dimethylaminopyridine (DMAP) or 1,3-dicyclohexyl carbodiimide (DCC).

9. A composition for diagnosis or therapy of cancer which comprises the conjugate of claim 1.

10. A composition for diagnosis or therapy of cancer which comprises the conjugate of claim 4.

\* \* \* \* \*

UNITED STATES PATENT AND TRADEMARK OFFICE
CERTIFICATE OF CORRECTION

| | | |
|---|---|---|
| PATENT NO. | : 8,946,394 B2 | Page 1 of 1 |
| APPLICATION NO. | : 13/877162 | |
| DATED | : February 3, 2015 | |
| INVENTOR(S) | : Kun Na et al. | |

It is certified that error appears in the above-identified patent and that said Letters Patent is hereby corrected as shown below:

Title Page, Item 73: "Gyeonggi-Do" should be -- Gyeonggi-do --.

In the Specification

Column 4, line 5: "IoN of nano-microspheres" should be -- 10μg of nano-microspheres --.

Signed and Sealed this
Fifth Day of May, 2015

Michelle K. Lee
*Director of the United States Patent and Trademark Office*